United States Patent
Bernhardt et al.

(10) Patent No.: US 8,825,139 B2
(45) Date of Patent: Sep. 2, 2014

(54) METHOD FOR AUTOMATIC DETECTION OF A CONTRAST AGENT INFLOW IN A BLOOD VESSEL OF A PATIENT WITH A CT SYSTEM AND CT SYSTEM FOR CARRYING OUT THIS METHOD

(75) Inventors: Dominik Bernhardt, Hausen (DE); Ute Feuerlein, Erlangen (DE); Stefan Großkopf, Nürnberg (DE); Michael Scheuering, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 393 days.

(21) Appl. No.: 13/093,213

(22) Filed: Apr. 25, 2011

(65) Prior Publication Data

US 2011/0263973 A1    Oct. 27, 2011

(30) Foreign Application Priority Data

Apr. 26, 2010 (DE) .......................... 10 2010 018 262

(51) Int. Cl.
*A61B 6/00* (2006.01)
*A61B 6/03* (2006.01)

(52) U.S. Cl.
CPC ............. *A61B 6/481* (2013.01); *A61B 6/5217* (2013.01); *A61B 6/541* (2013.01); *A61B 6/032* (2013.01); *A61B 6/488* (2013.01); *A61B 6/4441* (2013.01); *A61B 6/486* (2013.01); *A61B 6/4447* (2013.01); *A61B 6/482* (2013.01)
USPC ......................................................... 600/431

(58) Field of Classification Search
CPC ...... A61B 576/023; A61B 5/02; A61B 5/021; A61B 5/024; A61B 5/026; A61B 5/0275
USPC ...................... 600/431, 407; 378/21; 382/128
See application file for complete search history.

(56) References Cited

U.S. PATENT DOCUMENTS

2002/0151808 A1* 10/2002 Schwartzman et al. ...... 600/512
2003/0108149 A1*  6/2003 Tsuyuki ........................ 378/54

(Continued)

FOREIGN PATENT DOCUMENTS

CN      101523437 A      9/2009
DE  102007027366 A1    12/2007

(Continued)

OTHER PUBLICATIONS

T.F.Cootes, C.J.Taylor; Statistical models of appearance for medical image analysis and computer vision, In SPIE Medical Imaging, 4322 (2001) pp. 236-248; Others.

(Continued)

*Primary Examiner* — Tse Chen
*Assistant Examiner* — Joel F Brutus
(74) *Attorney, Agent, or Firm* — Harness, Dickey & Pierce, P.L.C.

(57) ABSTRACT

A method for automatic detection of a contrast agent inflow in a blood vessel of a patient with a CT system, and CT system for carrying out this method, are disclosed. At least one embodiment of the invention relates to a method which determines the position of at least one blood vessel in section image representations in a CT examination without external intervention with the aid of an active shape or active appearance model, measures the inflow of contrast agent in this region in a targeted way and automatically initiates at least one action in the event of inflowing contrast agent.

17 Claims, 4 Drawing Sheets

(56) References Cited

U.S. PATENT DOCUMENTS

| | | | |
|---|---|---|---|
| 2008/0292048 A1* | 11/2008 | Haras et al. | 378/20 |
| 2009/0002366 A1* | 1/2009 | Kanitsar et al. | 345/419 |
| 2009/0016587 A1* | 1/2009 | Strobel et al. | 382/130 |
| 2010/0046815 A1 | 2/2010 | Von Berg et al. | |

FOREIGN PATENT DOCUMENTS

| | | |
|---|---|---|
| DE | 102006040939 A1 | 3/2008 |
| DE | 102008048045 A1 | 4/2010 |
| JP | 2010000144 A | 1/2010 |

OTHER PUBLICATIONS

Cootes et al. Active Appearance Models Proceedings of the 5th European Conference on Computer Vision—vol. II—pp. 484-498; Others; 1998.

Aamexplorer, http://www2.imm.dtu.dk/~aam/aamexplorer/; Others. Dragos Datcu and Leon Rothkrantz, Facial Expression Recognition in still pictures and videos using Active Appearance Models. A comparison approach CompSysTech'07, pp. VI.13-1-VI.13-6, Rousse, Bugaria, 2007.; Others; 2007.

German Office Action dated Mar. 15, 2011 for German Application No. DE 10 2010 018 262.1.

Certified German Priority Application No. DE 10 2010 018 262.1 (not yet published).

Hauptkomponentenanalyse—Wikipedia; Hauptkomponentenanalyse—Wikipedia, http://de.wikipedia.org/w/index.php?title=Hauptkomponentenanalyse&oldid=72522285; Mar. 15, 2011.

Chinese Office Action issued in Application No. 2011101047656, dated Mar. 11, 2014.

* cited by examiner

METHOD FOR AUTOMATIC DETECTION OF A CONTRAST AGENT INFLOW IN A BLOOD VESSEL OF A PATIENT WITH A CT SYSTEM AND CT SYSTEM FOR CARRYING OUT THIS METHOD

PRIORITY STATEMENT

The present application hereby claims priority under 35 U.S.C. §119 on German patent application number DE 10 2010 018 262.1 filed Apr. 26, 2010, the entire contents of which are hereby incorporated herein by reference.

FIELD

At least one embodiment of the invention generally relates to a method for automatic detection of a contrast agent inflow in a blood vessel of a patient with a CT system, wherein monitoring scans are carried out in a predetermined region of the patient and, when a predetermined CT image value threshold is reached, these image values are output and/or an action is triggered.

At least one embodiment of the invention furthermore generally relates to a CT system having a scanner, a contrast agent applicator and/or a computer system for control and image evaluation with a memory for computer programs, the computer programs contained in the memory being carried out during operation.

BACKGROUND

Such methods and such CT systems are widely known. For instance, vascular diseases are diagnosed in modern medicine on the basis of computed tomography angiography (CTA) slice image data. For better recognition of vascular structures, a contrast agent is injected into the patient's veins when scanning a CTA. After a certain time, the contrast agent reaches the vessels to be imaged via the heart. Since the scan of the patient, during which he or she is moved on a support through the rotating gantry of the computer tomograph, takes a few seconds, the start of the scan must be matched in time to the instant of the contrast agent injection. To this end, in a predetermined slice, slice images are formed at a time interval of about 1 second and the blood vessels recognizable in the section are checked for inflow of contrast agent. If the contrast agent is visible owing to the local change in the image intensities, the scan can be automatically started.

A problem here is that when automating this procedure, before the inflow of contrast agent it is necessary to recognize where a blood vessel lies in the CT image. Since the blood vessels scarcely differ in their absorption from the surrounding organ, the known pattern recognition methods generally do not succeed in this case. In practice, it is therefore usually necessary for a doctor to observe the currently formed CT representations, recognize when an inflow takes place in a blood vessel and correspondingly give the start instruction for the actual CT scan.

SUMMARY

In at least one embodiment of the invention, a method is disclosed in which the intervention of a person with anatomical knowledge is no longer necessary in order to trigger a predetermined action automatically based on an inflow of contrast agent measured in an automatically found blood vessel.

In at least one embodiment a CT system is provided which carries out this method according to at least one embodiment of the invention.

Advantageous refinements of the invention are the subject-matter of dependent claims.

The Inventors have discovered the following:

In principle, it should be possible to ascertain the inflow of contrast agent from the differences between the individual images of an image sequence, since the image intensities change significantly only at the locations where the contrast agent flows through the blood vessels and therefore indicate the inflow of a contrast agent. A major difficulty, however, is that the patient moves during the observation phase, for example because of breathing, and displacements of the intensities recorded in the section image therefore take place. A further difficulty is that movement of a patient takes place not only in the recorded section plane but arbitrarily, so that, for example, bone material is now detected at locations where only tissue was previously detected, which respectively leads to a strong intensity increase at these positions of the image. Such misleading intensity differences due to patient movements can generally be excluded by registering the scan and restricting the search region. Furthermore, the inflow of contrast agent takes place with a slower and more constant rise compared with a change in the intensity due to movement. Furthermore, from the overall impression of the image, which a trained observer recognizes, it is easy to recognize a patient movement and therefore distinguish such changes from a contrast agent inflow.

An essential problem in the automatic detection of inflows is thus finding the correct region in a CT section representation, in which the blood vessel lies, even though blood vessels per se cannot readily be recognized in a CT representation owing to the similar absorption behavior of blood and tissue. The main problem thus resides in defining a position in a CT representation which, on the one hand, is subject to a certain degree of biological variability and, on the other hand, also varies from section image to section image owing to the patient's movement.

According to at least one embodiment of the present inventive concept, the Inventors propose to apply the basic principles, known per se, of an "active shape model" or, in an improved embodiment, the basic principles of an "active appearance model", to the present problem.

According to this basic principle of an "active shape model", in order to ascertain statistical average values, a multiplicity of CT representations are initially evaluated and characteristic anatomical structures, which are also easily recognizable by automatic methods, are determined in respect of their positions and subjected to a principal component analysis. In addition, the position of at least one blood vessel is also entered, which in the further course of the method is not recognizable in respect of its position by automatic recognition methods based on contrast differences.

A principal component analysis is thus carried out, into which the position data of the distinctive anatomical structures are entered as parameters, and an average value of these position data is determined. If the position of a blood vessel is now intended to be determined before a contrast agent inflow occurs, therefore before this blood vessel is recognizable merely on the basis of contrast differences, then automatic recognition of characteristic or distinctive anatomical structures is first carried out, which may be done for example by pattern recognition, and the positions of these distinctive anatomical structures are compared with the principal component analysis. A transformation vector is subsequently determined, with which the current representation is transposed onto the average model, and a comparison between the CT image values of the recorded time sequence on CT image representations is subsequently carried out on the basis of the known position of the at least one blood vessel at this location.

In an improvement of the "active shape model", it is also possible to use an "active appearance model" in which the grayscale values ascertained at the distinctive anatomical locations are included or at least the grayscale values at the position of the intended vessel are jointly included. With respect to these models, which are known per se, reference is made to the following publications, the entire content of each of which is hereby incorporated herein by reference:

> T. F. Cootes and C. J. Taylor, "Statistical models of appearance for medical image analysis and computer vision", in Proc. SPIE Medical Imaging, 2001;
>
> T. F. Cootes, G. J. Edwards, C. J. Taylor: "Active Appearance Models" in: H. Burkhardt, B. Neumann (eds), Proceedings of the European Conference on Computer Vision, Vol. 2, p. 484-498, Springer 1998;
>
> D. Datcu, L. J. M. Rothkrantz: "Facial Expression Recognition in still pictures and videos using Active Appearance Models. A comparison approach.", Proceedings of the 2007 international conference on Computer systems and technologies, Vol. 285, No. 112, 2007.

If the position of a blood vessel is thus defined in the manner mentioned above, with the aid of an "active shape model", or at least the ROI (ROI=region of interest) in which a blood vessel is meant to lie is determined, then the varying CT image values can be observed there and, based on the variation of the CT image values as a function of time, for example either the actual CT scan may be started, or, if the variation in the CT image values takes place too abruptly or too high a CT image value appears, it can be recognized that the supposedly found location of the blood vessel is not correct and instead the CT image values have changed owing to movement. If the "active appearance model" is used, in which the grayscale values of the CT representation are also included, then corresponding inflow can be inferred directly from the change in the parameters—without separate consideration of the CT image values.

According to this basic principle, the Inventors provide a method for automatic detection of a contrast agent inflow in a blood vessel of a patient with a CT system, which contains the following method steps:

providing statistical average values of principal components of a previous evaluation of a multiplicity of statistically comparable CT representations by at least two-dimensional position determination of distinctive points of anatomical structures including at least one blood vessel or an ROI for this blood vessel, carrying out one principal component analysis per CT representation and calculating the statistical average values of the principal components, carrying out a multiplicity of chronologically progressive scans in at least one predetermined section plane and progressive calculation of CT representations for the respective datum, at least two-dimensional automatic position determination of distinctive points of recognizable anatomical structures, with the exception of the at least one blood vessel or the ROI for this blood vessel, and determining the principal components, determining a deformation vector from the average principal components to the principal components currently ascertained for each CT representation and transformation (=image warping) of at least the position of the at least one blood vessel or the ROI for this blood vessel, determining a change in the image values as a function of time in the region of the at least one blood vessel or the ROI of this blood vessel over a multiplicity of CT representations at the respectively transformed positions of the at least one blood vessel or the transformed ROI for this blood vessel, and outputting the image values in the region of the at least one blood vessel or the ROI of this blood vessel and/or triggering an action if a predetermined first threshold of the image values is exceeded.

In addition to the positions of anatomical structures, CT image values of at least one anatomical structure may also be ascertained and processed in the principal component analysis.

In this case, it is possible for CT image values to be ascertained, and processed in the principal component analysis, exclusively at the position of the at least one blood vessel or the ROI.

As an alternative to this, CT image values may also be ascertained, and additionally processed in the principal component analysis, for a plurality of positions of anatomical structures of the at least one blood vessel or the ROI.

The Inventors furthermore propose that CT representations, which have been recorded in the absence of contrast agent in the bloodstream, be used to determine the average principal components. In this case, the at least one blood vessel or the ROI of this blood vessel may be ascertained manually in order to determine the average principal components.

According to another alternative, it is also possible for CT image representations, which have been recorded in the presence of contrast agent in the bloodstream, to be used to determine the average principal components. Since the blood vessels are also directly recognizable in this case, the at least one blood vessel and the ROI of this blood vessel may be determined automatically in order to determine the average principal components. In this context, it should be noted that it is particularly advantageous here for scans with different X-ray energies to be carried out in order to recognize the contrast agent and distinguish the contrast agent from, for example, bone structures, so that the positions of the contrast agent can be defined unequivocally on the basis of the different energy-specific absorption behavior of the contrast agent and bone.

In order to avoid false triggerings, it is also proposed that, if a predetermined second threshold, which is higher than the first threshold, of the image values at the at least one blood vessel or the ROI of this blood vessel is exceeded, the action triggered by the first threshold is stopped or not started.

In order to improve the automatic method, it is furthermore proposed that the positioning of the predetermined section plane can also be carried out with the aid of a previously recorded topogram and an automatic evaluation of this topogram.

In addition to the method according to at least one embodiment of the invention as described here, the Inventors also provide a CT system having a scanner, a contrast agent applicator and a computer system for control and image evaluation with a memory for computer programs, the memory of the computer system also containing programs which carry out the features of one of the methods described above during operation.

BRIEF DESCRIPTION OF THE DRAWINGS

The invention will be described in more detail below with reference to an example embodiment with the aid of the figures, only the features necessary for understanding the invention being represented. The following references are used: C1: CT system; C2: first X-ray tube; C3: first detector; C4: second X-ray tube (optional); C5: second detector (optional); C6: scanner; C7: C-arm; C8: displaceable patient support; C9: system axis; C10: computer system for control and image evaluation; C11: contrast agent applicator; C12: ECG lead; C13: memory; 1: topogram; 2: section plane; 3: average position of the aorta determined by an "active shape model" or "active appearance model"; 4: time profile of the CT values at the position 3; 5: threshold value of the CT image values; A: aorta; $L_R$ and $L_L$: lobes of the lung; P: patient; $Prg_1$ to $Prg_n$: computer programs; R: costal arches; ROI: region of interest; S: section image; t: time; T: triangulation lines, W: spinal column.

In detail.

DETAILED DESCRIPTION OF THE EXAMPLE EMBODIMENTS

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

Figure 1:
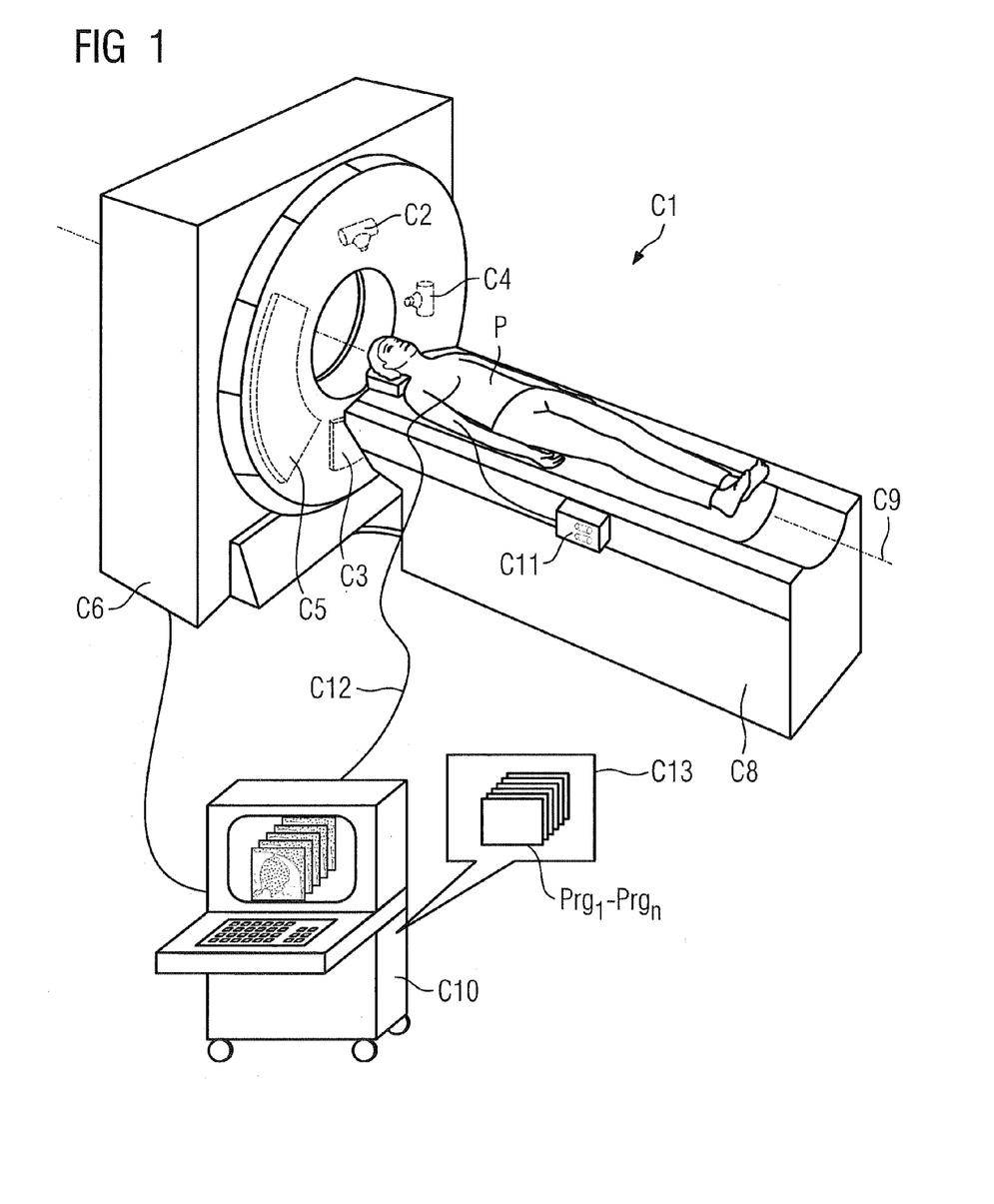
FIG. 1 shows a CT system for carrying out the method according to an embodiment of the invention.

FIG. 1 shows a CT system C1 according to an embodiment of the invention in an oblique schematic representation. This CT system C1 consists of a scanner C6, in which there is at least one X-ray tube C2 with a detector C3 lying opposite. Optionally, there may also be a further X-ray tube C4 and a further detector C5 on the gantry, so that simultaneous scans with different X-ray energies are also possible. A patient P lies on a patient support C8, which can be displaced along a system axis C9 and can be moved along the system axis C9 into the measurement region of the scanner C6 for the scan. A contrast agent applicator C11 is furthermore provided, which can deliver a contrast agent bolus when necessary and optionally under the control of the computer system C10. An ECG lead C12 is also provided, which optionally measures the heart activity and can also generate gated image data in a manner known per se. The computer system C10 has a memory C13, which may contain computer programs $Prg_1$ to Prg$_n$ that control the entire system, evaluate image data and also carry out the method according to an embodiment of the invention.

Figure 2:
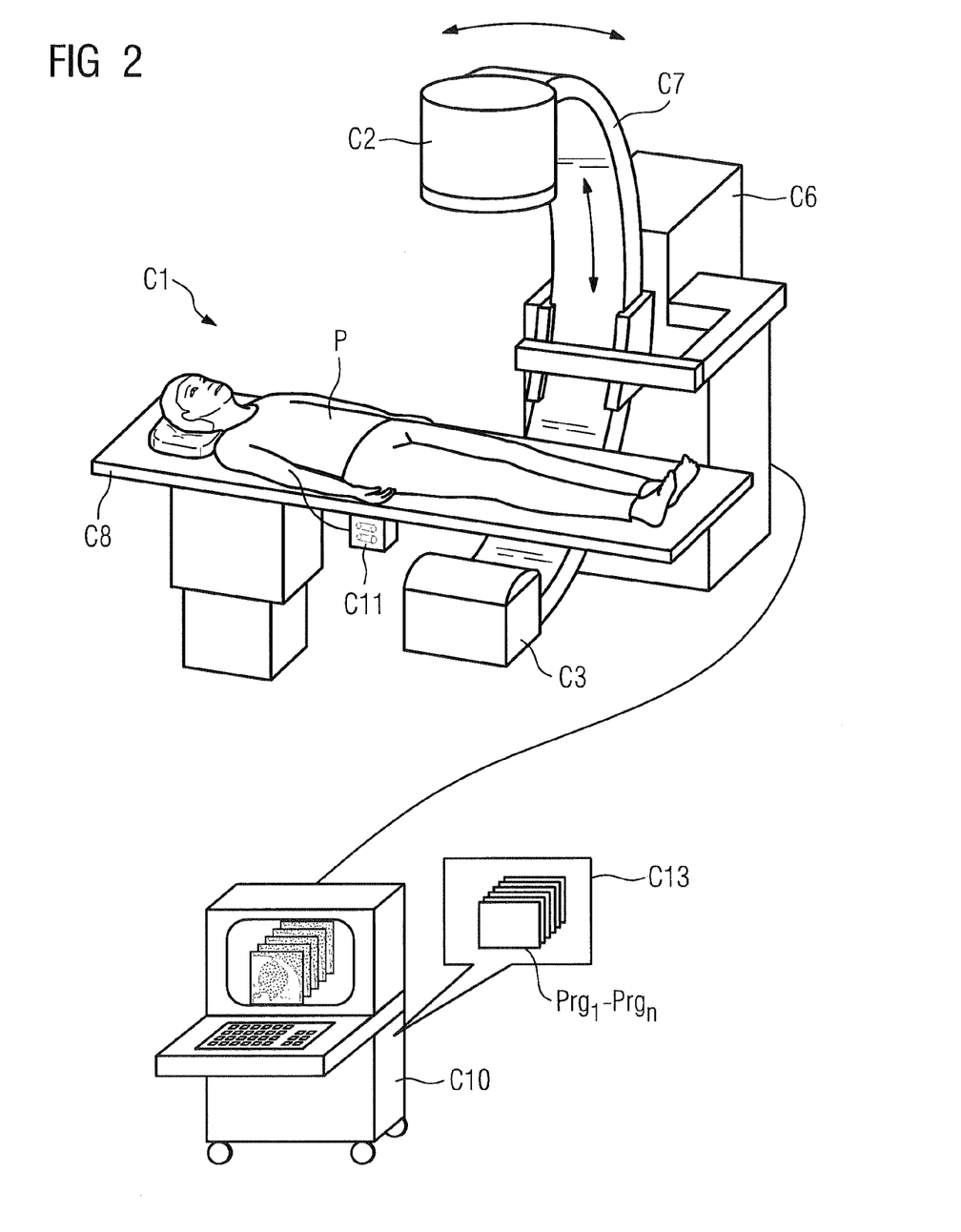
FIG. 2 shows a C-arm system for carrying out the method according to an embodiment of the invention.

Besides the CT system represented in FIG. 1 with a closed circular gantry, the method according to an embodiment of the invention described here may also be carried out with a C-arm system C1 as represented in FIG. 2. Such a C-arm system C1 likewise has a scanner C6 which, instead of a gantry, has a C-arm C7 at the ends of which an X-ray tube C2 and a detector C3 lying opposite are respectively arranged. A patient support C8 on which a patient P lies is furthermore provided, the C-arm C7 with the X-ray tube C2 and the detector C3 being tiltable about this patient P so as to scan this patient P. The entire system is controlled by a computer system C10 which, in a memory C13, contains computer programs Prg$_1$ to Prg$_n$ that are responsible for the control, the detector data evaluation and the image compilation. Furthermore, these programs can also carry out the method according to the invention. In addition, the C-arm system C1 represented here also has a contrast agent applicator C11 which, controlled by the computer system C10, can apply contrast agent into the bloodstream of the patient P when necessary.

Figure 3:
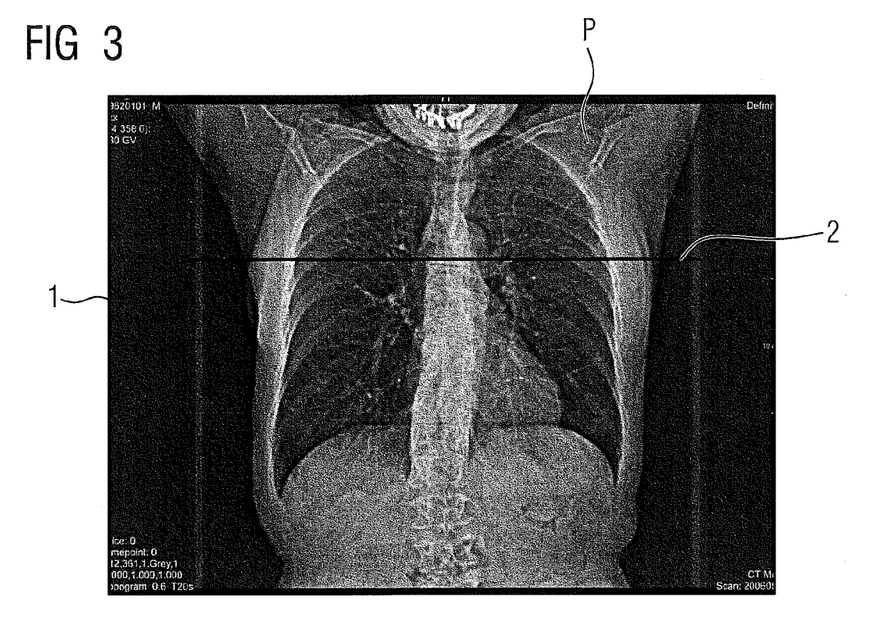
FIG. 3 shows a topogram with a selected section plane.
Figure 4:
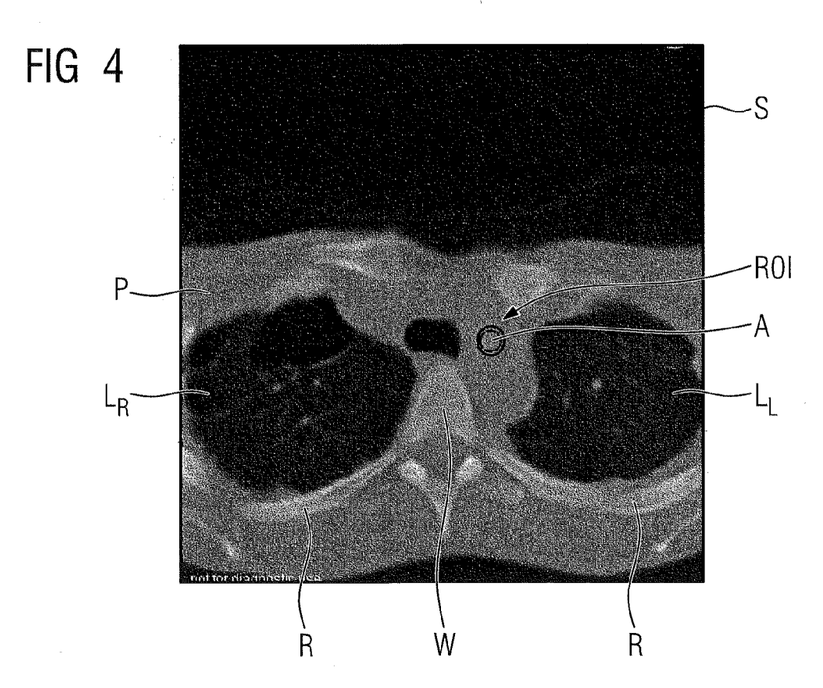
FIG. 4 shows a CT recording in the selected section plane of the topogram, recorded without contrast agent.

If a topogram 1 as shown in FIG. 3 is initially recorded by one of the CT systems presented above, then, with the aid of the anatomical features recognizable here, a section plane 2 in which the so-called "monitoring" takes place in the method according to an embodiment of the invention can be determined automatically with the aid of the computer system C10. Here, "monitoring" is intended to mean a time-offset circular scan which, while using minimal dosage, scans a particular section plane and generates CT section image representations S as shown in FIG. 4.

The cross section of the patient P in the section plane 2 of FIG. 3 can be seen in this section image representation S, the patient P being recognizable by means of distinctive anatomical structures, for example the lobes $L_R$ and $L_L$ of the lung which are represented as being dark. Bone structures, for example the spinal column W and the costal arches R, can also be recognized. Besides these distinctive recognizable anatomical structures, which form a corresponding contrast, the section image S also shows the aorta A which is surrounded by a circularly indicated region of interest ROI. The outer boundaries of the aorta A are represented by dashes. Since the contrast grading of this blood vessel in relation to the surrounding tissue is very weak, there is scarcely any possibility of representation without applying contrast agent, at least when using conventional CT systems which merely generate absorption representations. In particular, automatic detection of such blood vessels cannot be carried out.

Figure 5:
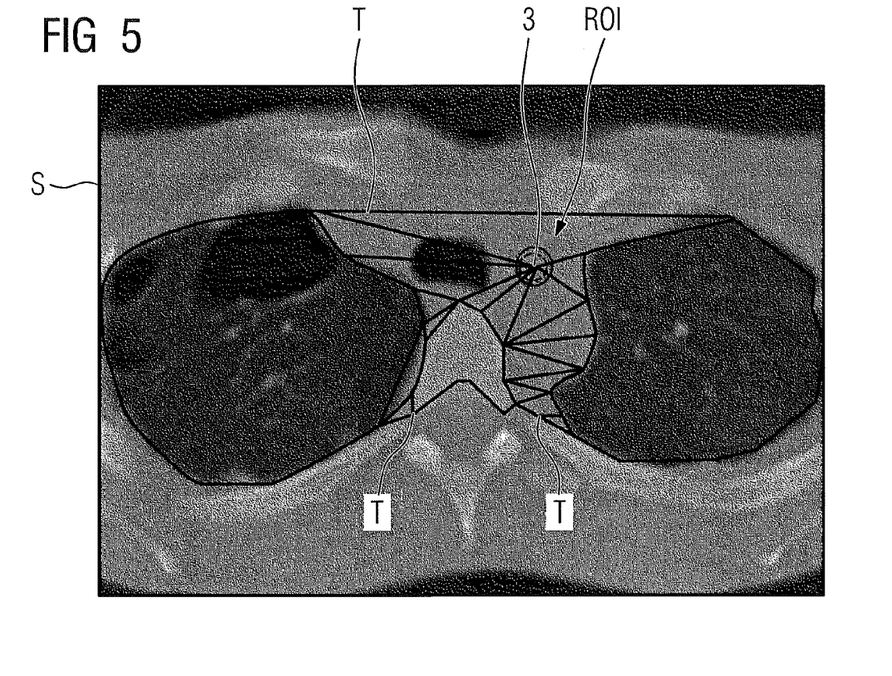
FIG. 5 shows a CT recording of FIG. 4 with triangulation lines and FIG. 6 shows a CT value/time diagram to represent the profile of a contrast agent inflow.

According to an embodiment of the invention, however, this positioning of the blood vessel is achieved—as represented in FIG. 5—by determining distinctive anatomical structures and their positions automatically in a manner known per se and statistically ascertaining their location relative to the aorta in a preliminary training phase. FIG. 5 again shows such a section image S, although here the distinctive anatomical structures have been automatically recognized and their positions and their characteristic positions have been connected together by triangulation lines T so that the relative position of the midpoint 3 of the aorta A or the ROI can be calculated. To this end, according to the invention, an "active shape model" is used so that movements of the patient which can lead to displacements of the distinctive anatomical structures can also jointly be taken into account and the respective current CT image can therefore be transposed onto the previously obtained central CT image, with its characteristic structures obtained in a principal component analysis.

Figure 6:
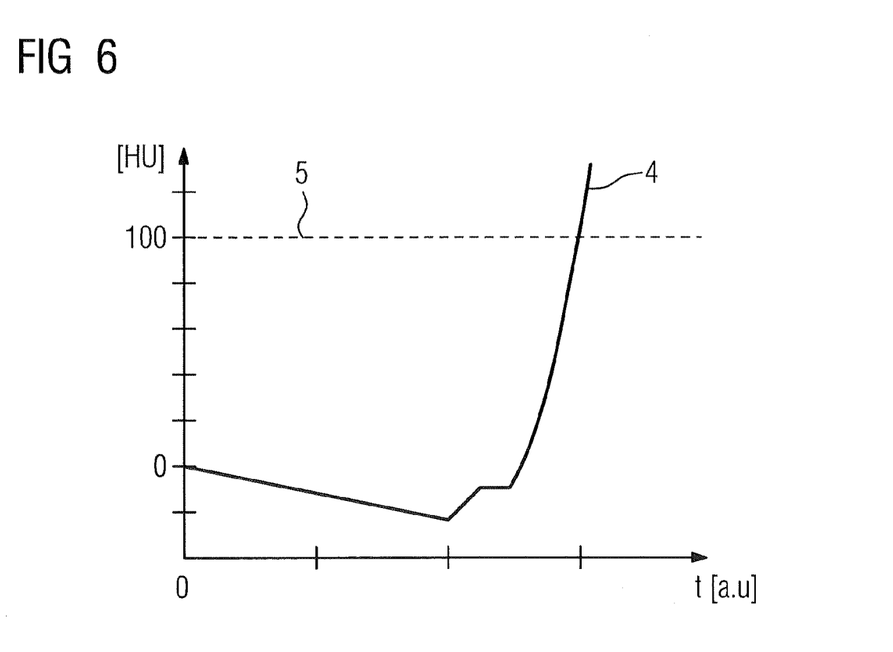

If the position 3 in a chronological sequence of CT representations is now considered and this is now plotted in a time-HU value diagram, then the time profile 4 of the HU values as shown in FIG. 6 is obtained. This FIG. 6 shows a diagram with the measured HU values on the ordinate and the time profile as a function of time t on the abscissa, as measured during a monitoring examination, for example at the position 3, of a section image S as shown in FIG. 5. In this case, the way in which there is a rather flat profile of the CT image values from left to right can be seen, which suddenly rises strongly on the right and thus signals inflow of the contrast agent in the aorta. As soon as a threshold value 5 is reached, according to the method according to the invention an action is triggered, for example the start of the actual CT scan in the presence of contrast agent in the scope of a CTA.

Overall, a method according to an embodiment of the invention is thus provided which determines the position of at least one blood vessel in section image representations in a CT examination without external intervention with the aid of an active shape or active appearance model, measures the inflow of contrast agent in this region in a targeted way and automatically initiates at least one predetermined action in the event of inflowing contrast agent.

It is to be understood that the features of the invention which have been mentioned above may be used not only in the combination respectively indicated, but also in other combinations or separately, without departing from the scope of the invention.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular' those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, tangible computer readable medium and tangible computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a tangible computer readable medium and is adapted to perform any one of the aforementioned methods when run on a computer device (a device including a processor). Thus, the tangible storage medium or tangible computer readable medium, is adapted to store information and is adapted to interact with a data processing facility or computer device to execute the program of any of the above mentioned embodiments and/or to perform the method of any of the above mentioned embodiments.

The tangible computer readable medium or tangible storage medium may be a built-in medium installed inside a computer device main body or a removable tangible medium arranged so that it can be separated from the computer device main body. Examples of the built-in tangible medium include, but are not limited to, rewriteable non-volatile memories, such as ROMs and flash memories, and hard disks. Examples of the removable tangible medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for automatic detection of a contrast agent inflow in a blood vessel of a patient with a computed tomography (CT) system, the method comprising:
providing, using a computer device, statistical average values of principal components of a previous evaluation of a multiplicity of statistically comparable CT representations by,
determining a multi-dimensional position of distinctive points of anatomical structures including a multi-dimensional position of at least one blood vessel or an ROI for the at least one blood vessel,
carrying out a per CT representation principal component analysis, and
calculating the statistical average values of the principal components;
carrying out, using the computer device, a multiplicity of chronologically progressive scans in at least one section plane;
progressively calculating, using the computer device, CT representations for respective datum;
determining, for each CT representation and using the computer device, a multi-dimensional position of distinctive points of recognizable anatomical structures, except with regard to the at least one blood vessel or the ROI for the at least one blood vessel;
determining, using the computer device, principal components for each CT representation;
determining, for each CT representation and using the computer device, a deformation vector from the statistical average values of the principal components to the determined principal components;
determining, for each CT representation and using the computer device, a transformation of the multi-dimensional position of the at least one blood vessel or the ROI for the at least one blood vessel;
determining, using the computer device, a change in image values as a function of time in a region of the at least one blood vessel or the ROI of the at least one blood vessel over a multiplicity of the CT representations at respectively transformed positions of the at least one blood vessel or transformed ROI for the at least one blood vessel; and
when a first threshold of the image values is exceeded, using the computer device to perform at least one of
outputting the image values in the region of the at least one blood vessel or the ROI of the at least one blood vessel, and
triggering an action.

2. The method as claimed in claim 1, wherein in addition to the positions of distinctive positions of recognizable anatomical structures, CT image values of at least one anatomical structure are also ascertained and processed in the principal component analysis.

3. The method as claimed in claim 2, wherein CT image values are ascertained, and processed in the principal component analysis, exclusively at the multi-dimensional position of the at least one blood vessel or the ROI.

4. The method as claimed in claim 2, wherein CT image values are ascertained, and additionally processed in the principal component analysis, for a plurality of positions of anatomical structures of the at least one blood vessel or the ROI.

5. The method as claimed in claim 2, wherein CT representations, which have been recorded without contrast agent in a bloodstream, are used to determine the statistical average values of the principal components.

6. The method as claimed in claim 5, wherein the at least one blood vessel or the ROI of the at least one blood vessel is ascertained manually in order to determine the statistical average values of the principal components.

7. The method as claimed in claim 2, wherein, if a second threshold, which is higher than the first threshold, of the image values at the at least one blood vessel or the ROI of the at least one blood vessel is exceeded, the action triggered by the first threshold is stopped or not started.

8. The method as claimed in claim 2, wherein the at least one section plane is automatically based on a previously recorded topogram.

9. The method as claimed in claim 1, wherein CT representations, which have been recorded without contrast agent in a bloodstream, are used to determine the statistical average values of the principal components.

10. The method as claimed in claim 9, wherein the at least one blood vessel or the ROI of the at least one blood vessel is ascertained manually in order to determine the statistical average values of the principal components.

11. The method as claimed in claim 1, wherein CT representations, which have been recorded with contrast agent in a bloodstream, are used to determine the statistical average values of the principal components.

12. The method as claimed in claim 11, wherein the at least one blood vessel or the ROI of the at least one blood vessel is determined automatically in order to determine the statistical average values of the principal components.

13. The method as claimed in claim 1, wherein, if a second threshold, which is higher than the first threshold, of the image values at the at least one blood vessel or the ROI of the at least one blood vessel is exceeded, the action triggered by the first threshold is stopped or not started.

14. The method as claimed in claim 1, wherein the at least one section plane is automatically based on a previously recorded topogram.

15. A computed tomography (CT) system, comprising:
a scanner;
a contrast agent applicator; and
a computer system for control and image evaluation, including a memory containing computer programs to, when executed, carry out a method including:
providing statistical average values of principal components of a previous evaluation of a multiplicity of statistically comparable CT representations by,
determining a multi-dimensional position of distinctive points of anatomical structures including a multi-dimensional position of at least one blood vessel or an ROI for the at least one blood vessel,
carrying out a per CT representation principal component analysis, and
calculating the statistical average values of the principal components;
carrying out a multiplicity of chronologically progressive scans in at least one section plane;
progressively calculating CT representations for respective datum;
determining, for each CT representation, a multi-dimensional position of distinctive points of recognizable anatomical structures, except with regard to the at least one blood vessel or the ROI for the at least one blood vessel;
determining the principal components for each CT representation;
determining, for each CT representation, a deformation vector from the statistical average values of the principal components to the principal components;
determining, for each CT representation, and a transformation of the multi-dimensional position of the at least one blood vessel or the ROI for the at least one blood vessel;
determining a change in image values as a function of time in a region of the at least one blood vessel or the ROI of the at least one blood vessel over a multiplicity of the CT representations at respectively transformed positions of the at least one blood vessel or transformed ROI for the at least one blood vessel; and
when a first threshold of the image values is exceeded, at least one of outputting the image values in the region of the at least one blood
vessel or the ROI of the at least one blood vessel, and triggering an action.

16. A non-transitory computer readable medium including program segments for, when executed on a computer device, causing the computer device to perform a method including:
providing statistical average values of principal components of a previous evaluation of a multiplicity of statistically comparable computed tomography (CT) representations by,
determining a multi-dimensional position of distinctive points of anatomical structures including a multi-dimensional position of at least one blood vessel or an ROI for the at least one blood vessel,
carrying out a per CT representation principal component analysis, and
calculating the statistical average values of the principal components;
carrying out a multiplicity of chronologically progressive scans in at least one section plane;
progressively calculating CT representations for the respective datum;
determining, for each CT representation, a multi-dimensional position of distinctive points of recognizable anatomical structures, with the exception of the at least one blood vessel or the ROI for the at least one blood vessel;
determining the principal components for each CT representation;
determining, for each CT representation, a deformation vector from the statistical average values of the principal components to the principal components;
determining, for each CT representation, a transformation of at least the multi-dimensional position of the at least one blood vessel or the ROI for the at least one blood vessel;
determining a change in the image values as a function of time in the region of the at least one blood vessel or the ROI of the at least one blood vessel over a multiplicity of the CT representations at the respectively transformed positions of the at least one blood vessel or the transformed ROI for the at least one blood vessel; and
when a first threshold of the image values is exceeded, at least one of
outputting the image values in the region of the at least one blood vessel or
the ROI of the at least one blood vessel, and triggering an action.

17. The non-transitory computer readable medium of claim 16, wherein in addition to the positions of distinctive positions of recognizable anatomical structures, CT image values of at least one anatomical structure are also ascertained and processed in the principal component analysis.

* * * * *